(12) United States Patent
Jung et al.

(10) Patent No.: US 9,895,553 B2
(45) Date of Patent: Feb. 20, 2018

(54) COLLIMATOR FOR FLOW PIXEL PROTON THERAPY

(71) Applicant: CATHOLIC UNIVERSITY INDUSTRY ACADEMIC COOPERATION FOUNDATION, Seoul (KR)

(72) Inventors: Joo Young Jung, Seoul (KR); Do Kun Yoon, Gyeonggi-do (KR); Tae Suk Suh, Seoul (KR)

(73) Assignee: The Catholic University of Korea Industry—Academic Cooperation Foundation, Seoul (KR)

( * ) Notice: Subject to any disclaimer, the term of this patent is extended or adjusted under 35 U.S.C. 154(b) by 0 days.

(21) Appl. No.: 14/898,240

(22) PCT Filed: Jul. 1, 2014

(86) PCT No.: PCT/KR2014/005865
§ 371 (c)(1),
(2) Date: Dec. 14, 2015

(87) PCT Pub. No.: WO2015/012505
PCT Pub. Date: Jan. 29, 2015

(65) Prior Publication Data
US 2016/0136457 A1    May 19, 2016

(30) Foreign Application Priority Data

Jul. 25, 2013    (KR) .......................... 10-2013-0087840

(51) Int. Cl.
*A61N 5/10* (2006.01)
*G21K 1/04* (2006.01)

(52) U.S. Cl.
CPC .......... *A61N 5/1045* (2013.01); *G21K 1/046* (2013.01); *A61N 2005/1087* (2013.01)

(58) Field of Classification Search
USPC ........ 250/505.1, 492.3, 492.1; 378/147, 148, 378/152
See application file for complete search history.

(56) References Cited

U.S. PATENT DOCUMENTS 4,987,309 A *   1/1991   Klasen ................. A61N 5/1042
                                                    250/492.1
8,637,841 B2 *   1/2014   Prince ................... G21K 1/046
                                                    250/492.1

FOREIGN PATENT DOCUMENTS

JP        472664262 B2      7/2011
JP        2012-058154 A     3/2012
(Continued)

*Primary Examiner* — Kiet T Nguyen
(74) *Attorney, Agent, or Firm* — Huffman Law Group, PC

(57) ABSTRACT

A collimator for flow pixel proton therapy providing an irradiation region which controls an intensity of an irradiated proton, including micro-motors arranged at both sides of a main frame connected, one to one, to multiple spread panels arranged in a center opening of the main frame by a corresponding ones of multiple elastic reels, in which a first half of the spread panels are moved to a first side of the main frame and a second half of the spread panels are moved to a second side of the main frame by the opposite micro-motors when a corresponding elastic reel is wound by a corresponding micro-motor, and in which each spread panel is in a stress release state when the corresponding elastic reel is unwound.

10 Claims, 7 Drawing Sheets

(56) References Cited

FOREIGN PATENT DOCUMENTS

| KR | 10-2009-0093654 A | 9/2009 |
| KR | 10-2010-0074566 A | 7/2010 |

* cited by examiner

[FIG. 1]
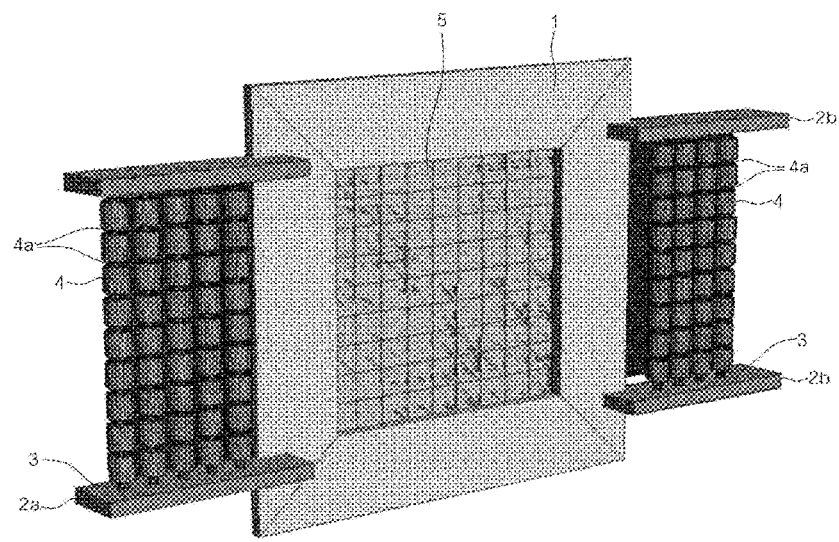
[FIG. 2]
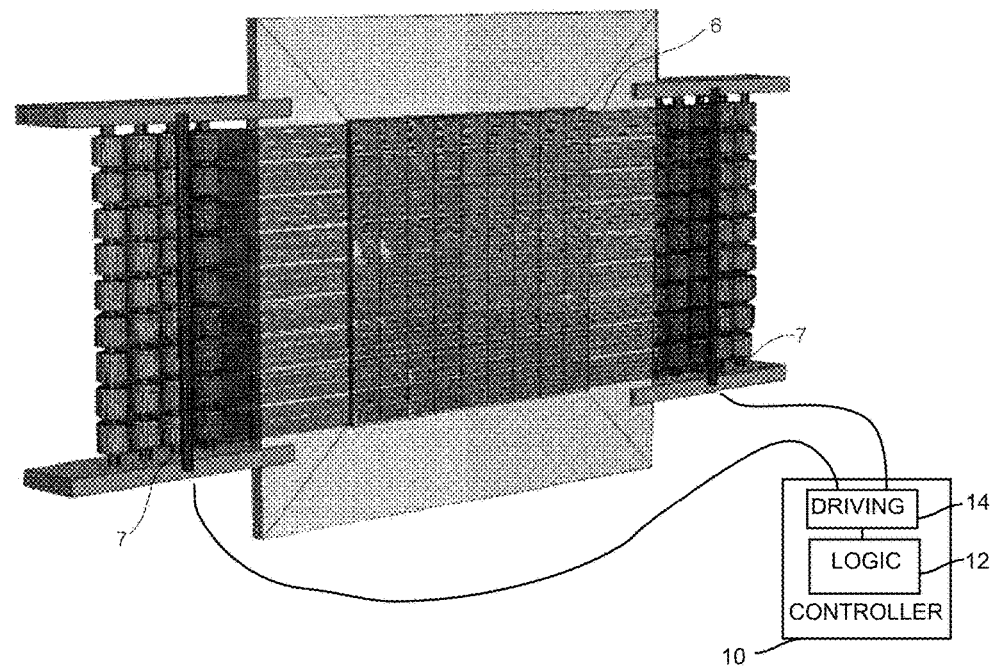

[FIG. 3a]
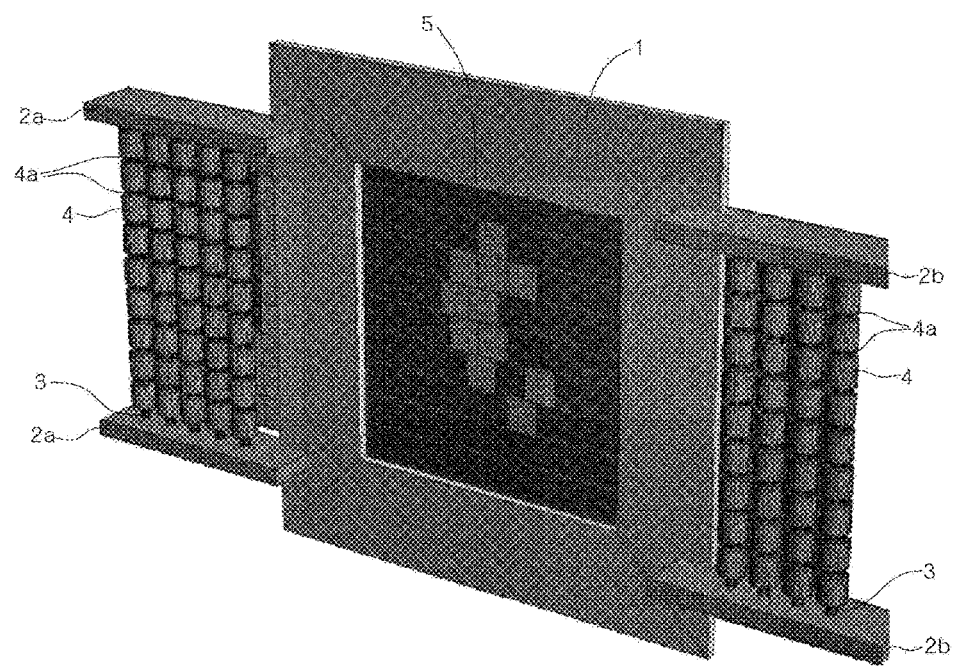

[FIG. 3b]
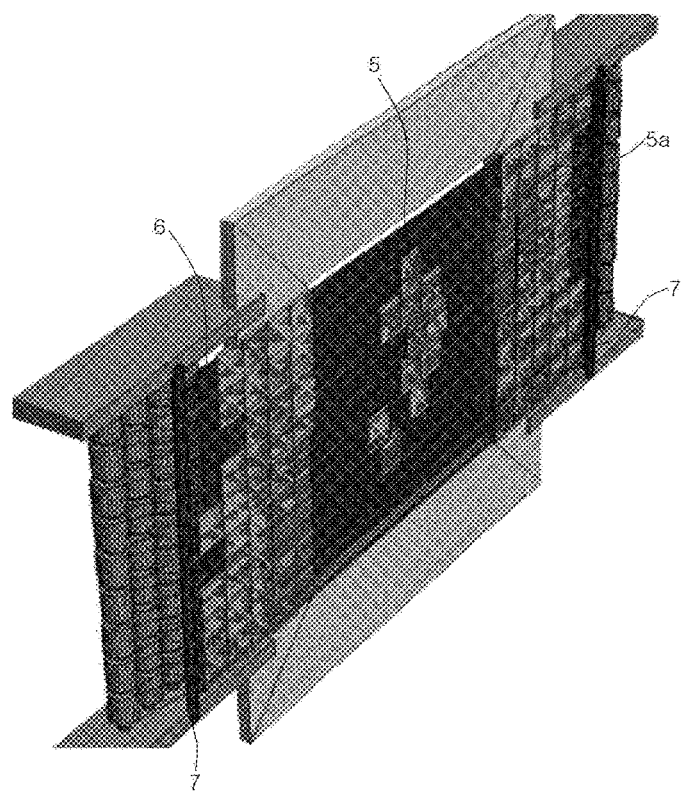
[FIG. 4a]
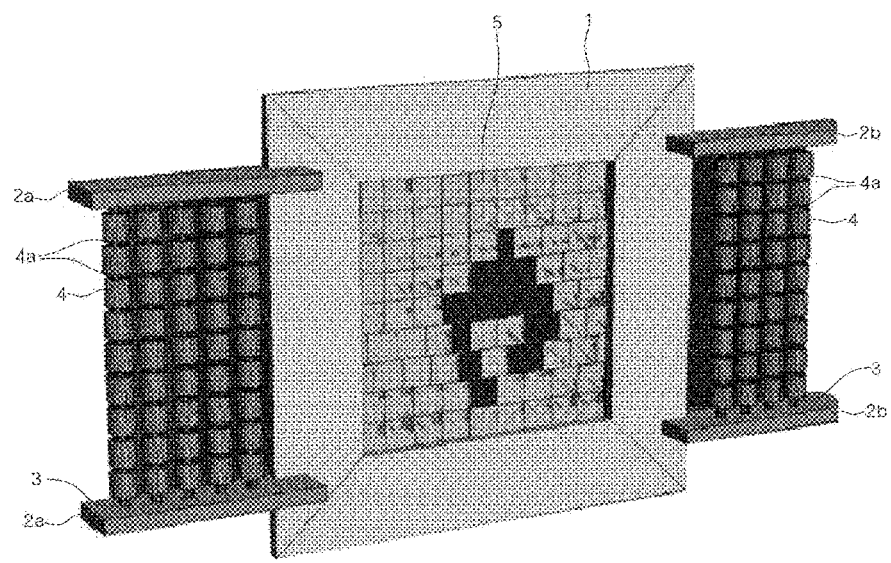

[FIG. 4b]
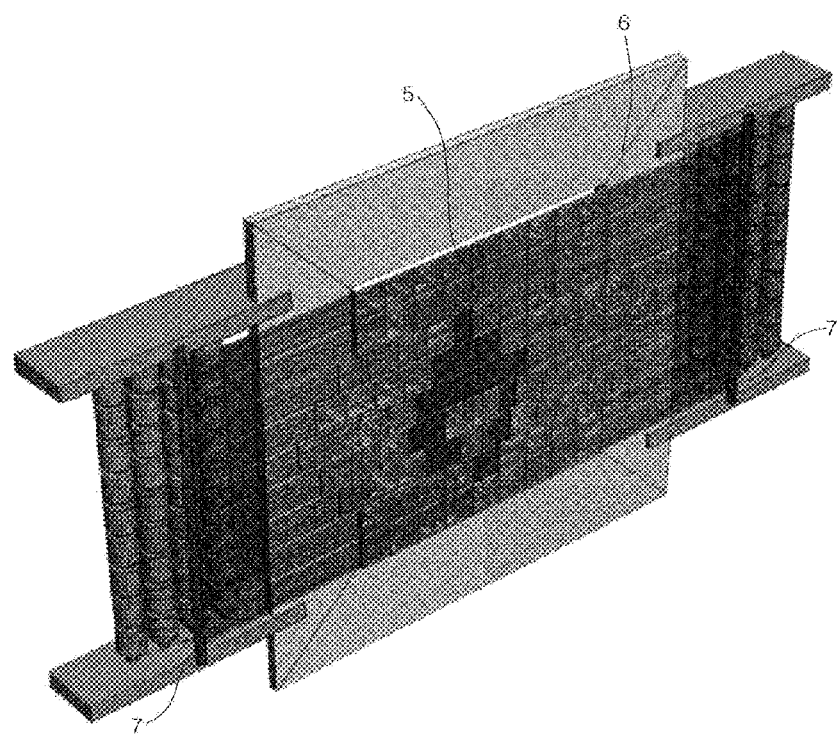
[FIG. 5a]
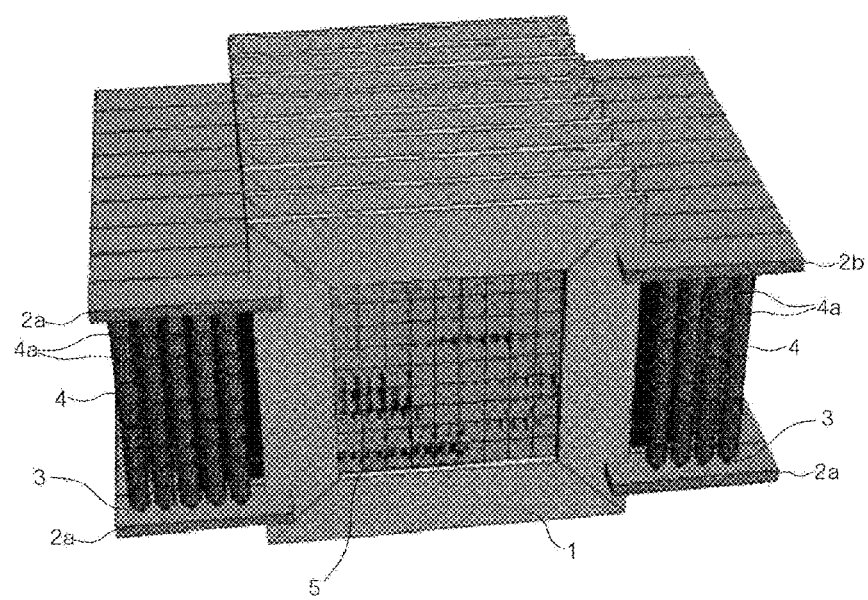

[FIG. 5b]
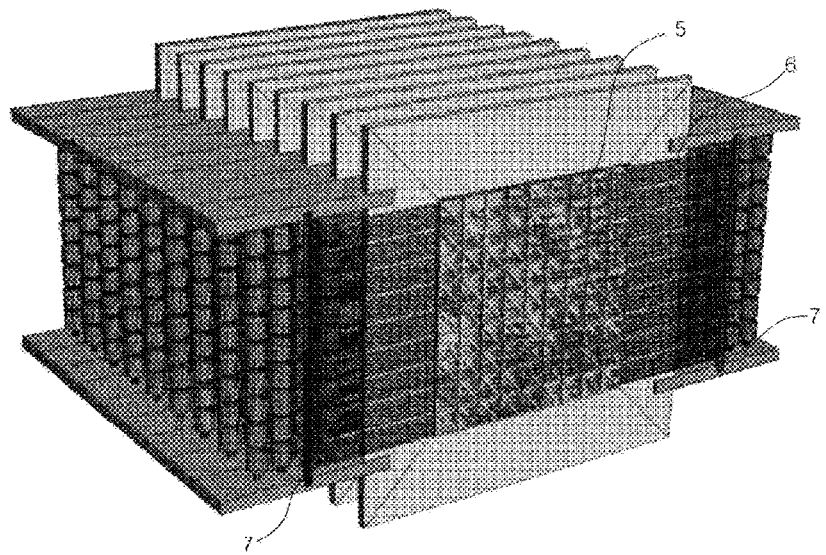
[FIG. 6]
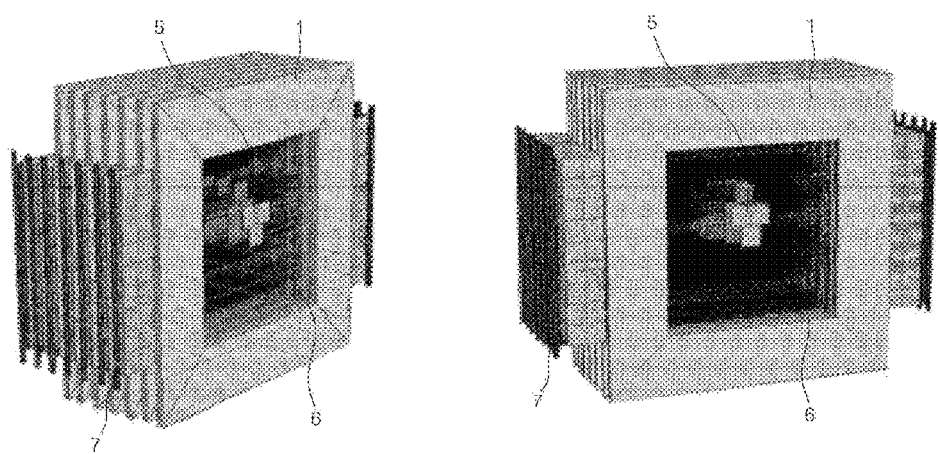

[FIG. 7a]
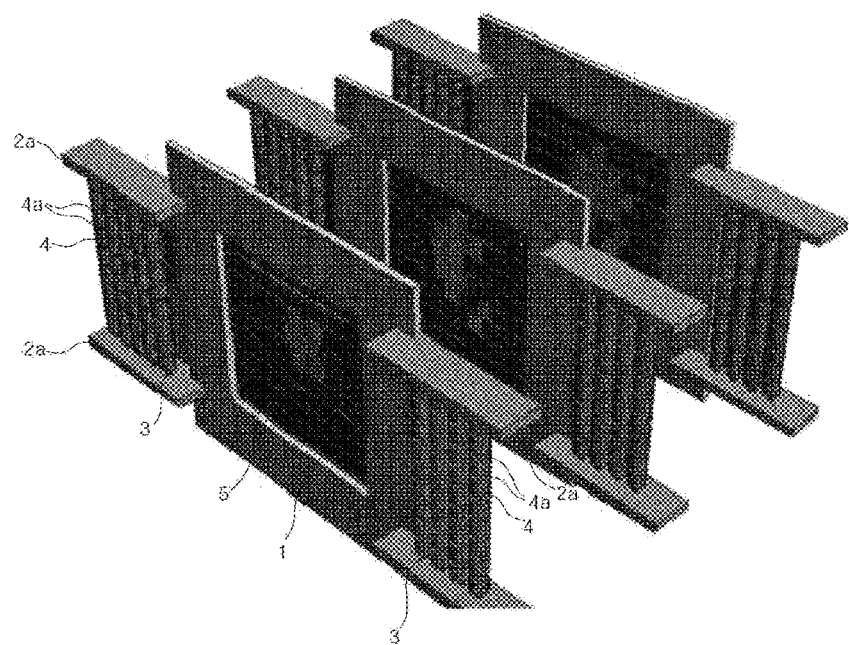
[FIG. 7b]
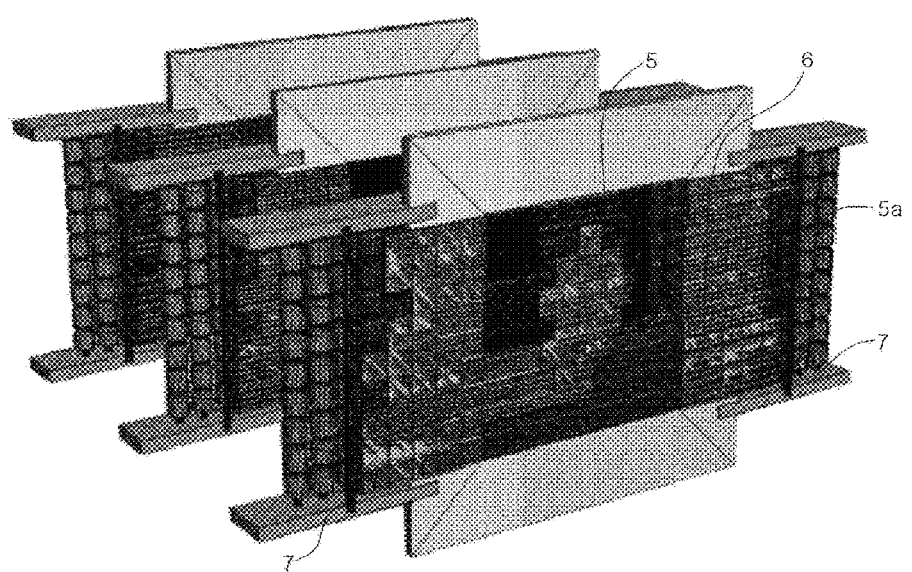

【FIG. 8】
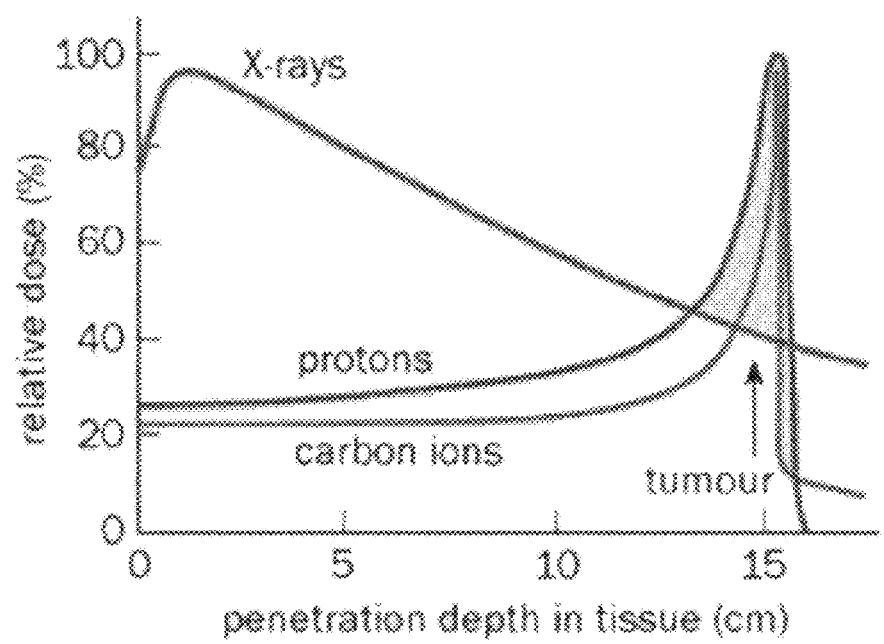
【FIG. 9】
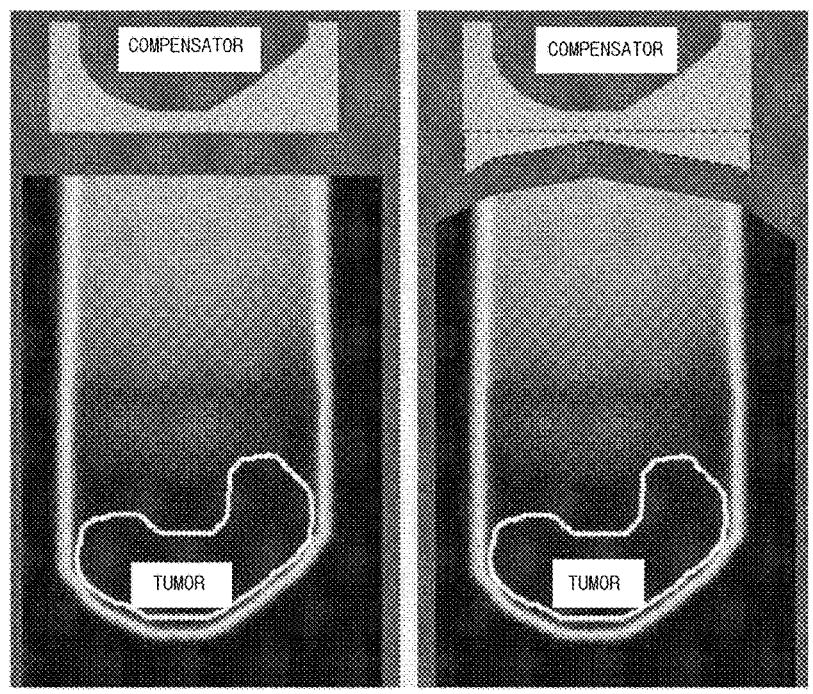

COLLIMATOR FOR FLOW PIXEL PROTON THERAPY

TECHNICAL FIELD

The present invention relates to a collimator for flow pixel proton therapy, specifically, to a collimator for flow pixel proton therapy, which is manufactured to allow the proton be correctly irradiated only on a tumor to be treated by arranging a plurality of spread panels in the form of pixel in the opened center of the main frame which becomes a proton irradiation region, arranging a plurality of micro-motors connected to each of the spread panel by an elastic reel, one to one, based on the far side to each other in both sides of said main frame, selectively moving each of the spread panels in or out of irradiation region of the radiation through the elastic reel with driving of each of micro-motors by a controller to allow the proton be correctly irradiated only on a tumor to be treated.

BACKGROUND ART

There is a need for controlling a dose of irradiation in a radiotherapy such as X-ray or gamma-ray and thus, a so-called collimator(collimator) is used. A representative form of this collimator is a multi-leaf collimator and this traditional multi-leaf collimator uses a driving mode wherein a plurality of leafs are moved individually, a dose of the radiation maintains or modifies a specific shape of the region to be delivered as a space form, and the dose is deliverd as time-based movement.

The said traditional multi-leaf collimator is necessarily attached to and used in almost all radiotherapy instruments in a radiation therapy at present, but there is an inconvenience that a plurality of leafs(leaf) are operated by seperately and directly moving. In addition, the said multi-leaf collimator is expensive as an imported article, is dificult to be self-produced, and when it is attached to and used in the radiation therapy, a plurality of leafs(leaf) maintain the space form by moving them every movement, but they do not change their position, only except for changing the said space form in place.

Therefore, it is ungent to introduce the technology into Korea, which can display a high performance per price in a formation of a complex dose region, or a control of a short or irregular dose intensity, as an instrument which can be manufactured by only Korean technology, and display the same degree of performance at a very lower price than the multi-leaf collimator.

Furthermore, when radition beams are passed by a plurality of leafs(leaf) in the traditional collimator, since the beams tend to spread as being far away, the spreading angle and an energy property should be considered, but said multi-leaf collimator does not consider these facts, and thus it leaves something to be desired in a delivery of the correct dose and intensity of radiation.

In addition, a particle radiation such as a proton beam or carbon ion beam has a specific dose delivery property such as Bragg peak(Bragg peak) unlike X-ray and thus has an advantage for protecting the around normal organs simultaneously with delivering much dose of radiation to the tumor. That is, as shown in FIG. 8, when considering the property of dose delivery of the particle radiation in a center, an Energy-transfer near the surface of medium greatly occurs in X-ray, but a high Energy-transfer (Bragg peak) occurs only in the special depth in the particle beam.

And, the particle radiation therapy generally treats a patient by spatially modulating the particle beam through dual scattering and range modulation(range modulation) mode for depth of penetration of beam. In this case, since forms of tumors are different from every patient, the particle radiation therapy uses a compensator regulating a distribution for the depth of penetration of the particle radiation in order to deliver the radiation dose only to a target. The particle radiation passing through a thin place of thickness of the compensator penetrates to a deep place in a body and since the depth of penetration becomes shallow in the body when passing through a thick place, the distribution of the radiation dose becomes coincident with the form of a depth direction of a tumor. That is, as shown in FIG. 9, since the depth of penetration of the particle beam in the body becomes deeper in the place wherein the thickness of compensator is shallow, and the depth of penetration becomes shallow in the place wherein the thickness of compensator is thick, the distribution for the depth direction of the radiation dose can be regulated.

In the above compensator, a traditional compensator processes solid polymer materials such as PMMA (Polymethyl Methacrylate) and the like or soft materials such as wax and the like by using a milling machine to fit to the treatment site of the patient and use it in the treatment of the patient. But, since such the compensator is patient-specific, it should be individually produced for each patient, and cannot be reused in other patient after the treatment, as well as even in the same patent, when the beam direction used in the treatment is increased, the same number of compensators should be produced. Therefore, the continuously high expenditure for the material cost is occured, and since the time required for manufacturing the compensator is too long, there are problems in treating many patients at the same time or in rapidly treating the emergency patient. In addition, when two or more of beams are used, there is a risk that a treatment is to be made while reversing compensators each other by a human error.

As mentioned above, since the proton therapy should produce and use high energy protons, it cannot be used in a hospital equiping with a seperate production facility. In addition, although the proton treatment is possible, in order to compose the dose distribution necessary for the tumor tissue via a treatment plan, the corresponding compensator and damping material being optimized to the tumor tissue shoud be produced, but it is the form wherein the treatment is made after the production period for 1 day normally as often, for 3 days when delaying. Although the problem of delaying is a part being resolved by the normal effort, there is an inconvience that all damping materials suitable for tumor tissues should be produced in each patient.

SUMMARY

Technical Problem

The present invention is designed to improve all sorts of the problems as mentioned above, and its object is to provide a collimator for flow pixel proton therapy, comprising a main frame wherein the opened center becomes a proton irradiation region, a plurality of spread panels in the form of pixel arranged in the center of the main frame, a plurality of micro-motors connected to each of the plurality of spread panel by an elastic reel, one to one, based on the far side to each other by arranging in both sides of said main frame and controller, wherein the irradiation region is made by selectively moving each of the spread panel through the elastic reel with driving the micro motor by the controller to control the intensity of the proton irradiated for treating the tumor.

In the above, the plurality of micro motors arranged in both sides divide the center of the spread panel in half and connect them to the spread panel far from each other, but, all of the center of the spread panel which is connected to the micro-motor by the elastic reel and divided in half allows the state completely moved to the micro motor at both sides, by the micro-moter, be in a stress release state of being unwound by the elastic reel.

Another object of the invention is to provide a collimator for flow pixel proton therapy, comprising the multi-layer collimator made by laminating a number of main frame installed with the spread panel connected by the elastic reel and the micro-motor, wherein the multi-layer collimator can be also used as the collimator comprising the irradiation region transmitting the radiation.

Technical Solution

In order to achieve the objects mention above, the collimator for flow pixel proton therapy of the present invention is characterized in that in the collimator comprising the irradiation region for controlling the intensity of protons to be irradiated by directing shapes of various spaces, a plurality of micro-motors arranged at both sides and a plurality of spread panels arranged in the center are connected to each other, one to one, by the elastic reel, relatively far micro-motors and spread panels are connected to each other by a ratio of the same number, and the plurality of spread panels arranged in the center, the state are divided in half and moved to both sides by the opposite micro-motors, are allowed, by the micro-motors, to be in a stress release state of being unwound by the elastic reel.

Also, it is preferable that the opened center further comprises the main frame becoming the proton irradiation region and the connection frame connected to both sides of the main frame, and thus, a plurality of micro-motor installed by supporting by the supporter connected to both sides of the connection frame, and the spread panel in the form of pixel arranged in the center of behind side of the main frame are connected to each other by the elastic reel, and the driving of each micro-motor is controlled by the controller so as to wind or unwind the elastic reel to selectively move the plurality of the spread panels.

Also, it is preferable that the said supporter is multiply connected by putting side by side spacing apart between top and bottom of the connection frame, the micro-motor is multiply arranged in top and bottom through a plurality of each supporter, and the each elastic reel connects between the motor axis of each micro-motor in the distance to the nearest and each spread panel.

Also, it is preferable to further comprise the reel guide which is installed for a tension of the elastic reel in each connection frame between the macro-motor in both sides of the main frame and spread panel to allow the elastic reel pass over it.

Also, it is preferable that a plurality of each spread panel moved by each micro-motor and the elastic reel is allowed be moved to out of the opened center which becomes the proton irradiation range of the main frame, and the elastic reel is comprised of the materials which are not affected by the radiation reaction.

Also, it is preferable that the controller is equipped with a logic circuit and driving circuit consisted of a program, the micro-motor for the movement of each spread panel is allowed to drive by receiving a signal from the driving circuit directly connected to the logic circuit, the micro-motor is equipped with the motor axis in both sides and connects the spread panel to between each motor axis and the spread panels by two (2) elastic reel, and the outer side around each motor axis is formed in the form of saw tooth.

Also, it is preferable that the micro-motor connected by the elastic reel and the main frame installed by the spread panel are multiply laminated to install multi-layer of collimator, and the multi-layered collimator is used as the collimator comprising the irradiation region transmitting the radiation by directing shapes of various space.

Advantageous Effects

According to the collimator for flow pixel proton therapy of the present invention, there is an effect that the manufacturing mode of a damper and a compensator for proton therapy, which have been conventionally manufactured by hand, is provided to use reverse collimation mode through a collimator, thereby collimating spread panels at a section requiring the spread at the Bragg peak, determining the shape of the section and a damping section through a program, and applying the same to tumor treatment.

By the above, the present invention has greatly another three (3) effects over the traditional methods, as follows.

At first, the damper and the compensator used in the traditional proton therapy are to be spend the cost due to the manufacture by hand, has the corresponding time delay and to be put the workers, but since the collimator of the present invention can be operated by digitalized and automated mode, it has the effects preventing the cost for manufacturing the damper and the compensator by hand, the delay of time and the waste by putting the workers.

Secondly, in the case of that the correction is needed due to the movement of the patient, or a sharp deformation of the tumor shape and the error of an interim treatment schedule, the collimator of the present invention has a powerful compatibility which can change the irradiation region by the spread panel in real-time to fit the treatment schedule according to the program installed on the controller constituting the collimator.

Thirdly, the collimator of the present invention has the effect which can be mechanically designed by a simple and efficient manner over the hardware designed to fit the damper and compensator traditionally used.

BRIEF DESCRIPTION OF THE DRAWINGS

FIG. 1 is a front perspective view of one embodiment of a collimator for flow pixel proton therapy.

FIG. 2 is a behind perspective view of the collimator of FIG. 1. FIG. 3a is a front perspective view of a use state of the collimator, showing an irradiation region for the proton therapy in some of the center by moving some of the spread panels to both sides.

FIG. 3b is a behind perspective view of the use state of the collimator also illustrated in FIG. 3a.

FIG. 4a is a front perspective view of a general collimation mode of the collimator, showing an irradiation region for the penetration of the radiation by moving the spread panel except for some of the center.

FIG. 4b is a behind perspective view of the general collimation mode of the collimator.

FIG. 5a is a front perspective view of one embodiment of a multi-layer collimator for flow pixel proton therapy for use in a multi-layered mode.

FIG. 5b is a rearward perspective view of the multi-layer collimator. FIG. 6 are perspective views depicting the actuation of the multi-layered collimator.

FIG. 7a is a front exploded view of the multi-layer collimator, revealing three different layers.

FIGS. 7b is a rear exploded view of the multi-layer collimator.

FIG. 8 is a graph showing the dose delivery property of a proton in a medium.

FIG. 9 is a comparison showing the changes in the depth of proton penetration into the human body depending on the thickness of a compensator.

DESCRIPTION

Hereinafter, explanation on preferred Examples of the collimator for flow pixel proton therapy according to the present invention will be given in detail with reference to the attached drawings. The present invention should not be construed as being limited into Examples disclosed below, but can be embodied by various forms to each other, provided that the present Examples are provided to complete the disclosure of the present invention and to completely notify the scope of the invention to the ordinary person in the art.

FIG. 1 is a front perspective view of the collimator for flow pixel proton therapy according to the present invention and FIG. 2 is a behind perspective view of the collimator for flow pixel proton therapy according to the present invention.

As represented in FIGS. 1 and 2, the collimator for flow pixel proton therapy according to the present invention has the basic constitution of main frame 1, connection frames 2a, 2b, supporter 3, micro-motor 4, spread panel 5, elastic reel 6 and a controller 10.

The main frame 1 is comprised of square frame the center of which is opened, thereby the opened center becomes the irradiation range irradiated by the proton, and the spread panel 5 in the form of pixel is basically arranged in the opened center.

The connection frames 2a, 2b are installed by connecting in a long plate shape from top to below of both sides of main frame 1, respectively, and fix the supporter 3 for installing the micro-motor 4.

The supporter 3 is multiply installed side by side over between each connection frame 2a, 2b, plays a role by connecting a plurality of micro-motors 4 installed side by side from top to below to each supporter 3 to each other, and fixes them.

Each of the micro-motor 4 is connected to the supporter 3 by connecting the motor axis 4 to the center of the top and below, respectively, and installs the same number of micro-motors 4 connected from top to below per each supporter 3.

The spread panel 5 is arranged in the center behind of main frame 1 in the form of pixel by connecting a plurality of panels top and bottom and left and right, forms one great spread range gathering a plurality of numbers of spread panels 5.

The elastic reel 6 is connected, by two (2) elastic reels, one to one, the motor axis 4a of both sides of the plurality of micro-motor 4 and between top and below of the plurality of spread panels, and the one side of main frame 1, i.e., micro-motor 4 located at the left side is connected to another side of the main frame 2, i.e., the spread panel 5 located at the right side at the rate of the same numbers. Wherein upon connecting two (2) elastic reels 2 are connected to the spread panel 5, two (2) elastic reels 6 are connected by penetrating through top and below of side of the spread panel 5, or is connected by attaching two (2) elastic reels 6 at top and below behind the spread panel 5.

For example, as in FIGS. 1 and 2, four (4) micro-motors 4 in the left of main frame 1 are connected to four (4) spread panels 5 in right of main frame 1, but is connected to each other, based on the near side to each other, four (4) micro-motors 4 in the right of main frame 1 are connected to four (4) spread panels 5 in the left of main frame 1, but is connected to each other, based on the near side to each other.

In this case, it is preferable that the outer circumference of the motor axis 4a is formed in the saw tooth shape to smoothly make the winding and unwinding of the elastic reel 6 wounded on the motor axis 4a of both sides of the micro-motor 4.

The controller 10 is likely a Personal Computer (PC) equipped with a logic circuit 12 and driving circuit 14 controlled by a program (not shown), it delivers the driving signal directly connected to the logic circuit 12 to each micro-motor 4, and thereby drives each of the micro-motor 4 to move each spread panel 5 via the elastic reel 6.

Meanwhile, it is preferable that in order to maintain the tension of each elastic reel 6 connecting between each of the micro-motor 4 and spread panel 5, each elastic reel 6 is connected via the reel guide 7, by installing a reel guide 7 with slightly apart from the micro-motor 4.

The followings will explain the use state of the collimator for flow pixel proton therapy together with the movement of the spread panel for composing the proton irradiation region.

FIG. 3a is the front perspective view of the collimator for flow pixel proton therapy of the present invention composing the irradiation region for the proton therapy in some of the center by moving some of the spread panels to both sides, FIG. 3b depicts the behind perspective view of the collimator for flow pixel proton therapy of the present invention composing the irradiation region for the proton therapy in some of the center by moving some of the spread panel to both sides.

The collimator for flow pixel proton therapy of the present invention composes the irradiation region of the proton by moving the relevant spread panel 5 with selectively winding or unwinding the elastic reel 6 by the driving of the micro-motor 4 according to the control of the controller.

That is, as depicted in FIG. 3a, when pulling the distal spread panel 5a into the center of the main frame 1 by selectively winding the elastic reel 6 with only micro-motor 4 connected the some spread panels 5 of the center and the elastic reel 6, under the state completely unwinding the elastic reel 6 to be in a stress releasing state being the state that all the spread panels 5a are completely moved at both sides of main frame 1, the center of the main frame 1 is arranged with some of the spread panels 5 and the other part becomes the empty space in which the spread panel is arranged.

When some of the spread panels 5 are arranged in the center, the intensity of the proton passing through the part on which the spread pane 5 is arranged in the proton irradiation range of the main frame 1 is decreased, and the intensity of the proton passing through the part which is empty becomes strong, and then the reverse collimation mode is composed.

When the driving of the micro-motor 4 is stopped after completing the proton treatment, the wound elastic reel 6 is automatically unwound, and the spread panel 5, which moved to the center of main frame 1, is in the stress release state wherein it moves to the both sides of the main frame 1 and falls.

FIG. 4a is the front perspective view of the collimator for flow pixel proton therapy of the present invention displaying the general collimation mode composing the irradiation region for the penetration of the radiation by moving the spread panel except for some of the center, and FIG. 4b is the behind perspective view of the collimator for flow pixel proton therapy of the present invention displaying the general collimation mode composing the irradiation region for the penetration of the radiation by moving the spread panel except for some of the center.

The collimator for the proton therapy of the present invention composes the irradiation region by selectively winding or unwinding the elastic reel 6 by the driving of the micro-motor 4 according to the controller to move the relevant spread panel 5.

That is, as depicted in FIG. 4a, when moving the distal spread panel 5 into the both sides of the main frame 1 by unwinding the elastic reel 6 with being stress releasing state in which only some spread panel 5a at both sides and the micro-motor 4 connected to the elastic reel 6 is slightly driving or is not completely driving, under the state completely winding the elastic reel 6 by the driving of the micro-motor 4 to be in a stress state being the state that all the spread panels 5 are completely moved to the center of main frame 1 and gathered, the center of the main frame 1 forms the empty space in which some of the spread panels are not arranged.

When the empty space in which some of the spread panels are not arranged in the center is formed, the radiation beam is passed through the empty part wherein the spread panel is not arranged within the radiation irradiation range of the main frame 1, and thereby the reverse collimation mode for radiation therapy is composed.

Like this, the collimator for proton therapy of the present invention is made by basically installing on the proton therapy instrument for treatment of the cancer patient so as to be correctly irradiated to only the tumor to be treated, and has the basic principle that the spread panel 5 which can change the shape of Bragg-peak curve of the proton by the power of the micro-motor 4 arranged in the outer of the proton-ray irradiation range of the main frame 1 by using the elastic reel 6 which does not react well with the proton. It composes the final shape of the spread in the suitable shape for the tumor tissue to be treated by moving a plurality of spread panels 5 not one spread panel at the same time.

Of course, the radiation treatment instrument for the radiation therapy can also install and use the collimator of the present invention, and the explanation for it is as above.

FIGS. 5a and 5b are the front and behind prospective views of the multi-layer collimator composing the collimator for flow pixel proton therapy of the present invention in the multi-layered mode.

As depicted in FIGS. 5a and 5b, the collimator for flow pixel proton therapy of the present invention can also compose the multi-layered collimator composed by laminating the main frame 1 in several folds, not one. When the main frame 1 is composed by laminating it in several folds, there is an advantage that the composition of the proton irradiation region can be stereoscopically formed. The movement of the spread panel 5 in each of main frame 1 is made by driving the micro-motor 4 connected to the spread panel 5 and elastic reel 6, as mentioned above.

FIG. 6 is the front and behind prospective views showing the actuation of the multi-layered collimator, and FIGS. 7a and 7b depict the front and behind views showing the movement of the collimator of each layer in the folded parts.

As depicted FIGS. 6, 7a and 7b, some of spread panels 5 in each layer are moved to both sides of the main frame 1, and some of spread panels 5 are arranged in the center of the main frame 1 by virtually applying the treatment schedule to the substantial proton therapy. That is, the remaining spread panels 5a except for the necessary spread panels 5 arranged in the center of the main frame 1 are moved to outer of the proton irradiation range so as not to affect the proton irradiation.

Like this, when the spread panels are multi-folded structure and are presented on the proton irradiation line, the effect increasing Bragg-peak spread interval of the proton as much can be made and it can be effectively applied to the composition of the dose distribution.

The major properties of such collimator of the present invention are as follows:

1) It is a spread panel which moves by the driving of the micro-motor connected to the elastic reel and by delivering the power to it.

2) It is a mode moving the spread panel in orthostyle in a holding status depending only on the elastic reel and drives a plurality of panels at the same time.

3) It is a constitution of the connection frame and supporter which can fix the movement in the stress releasing state for the spread panels to be outside of the proton-ray irradiation range.

The collimator of the present invention having said properties is the mode wherein Bragg-peak control mode of the proton can be controlled by the movement of collimator according to the program, not the direct manufacture of the damper structure. Since frequently in the proton therapy, the manufacture of the compensator and the substantial damper is affected, not the collimation mode such as the multi-leaf collimator as in the proton-ray therapy like the radiation, the collimator of the present invention has been designed to the effect that such inconvenient trouble is eased by introducing the new mode of collimator.

The operation mode of the collimator of the present invention has the basic operation mode being the mode that the elastic reel pulls the spread panel connected to the micro-motor as mentioned above, the shape is composed by the program so as to fit the interval to which Bragg-peak is to be applied by moving a plurality of spread panels at the same time, not one. Wherein the spread panel is the material decreasing the proton in the partial ratio and is the material having a substantial role in spreading Bragg-peak. It is manufactured to fit for the patient in normal proton therapy but, in the collimator of the present invention, it is operated by the system by dividing it with several pixels, controlling it by the controller programmed by the separate program, and then, directing the instruction so as to move for fitting the shape to be manufactured.

In addition, the spread panel is composed by the material which can spread Bragg-peak and is manufactured based on the specific shape and the basic shape of the basic rectangle. The spread panel is arranged in several pixel forms and the movement of the spread panels of all pixels is controlled by the elastic reel connected, the elastic reel is moved by the micro-motor on outside of the radiation irradiation range. One spread panel has only the linear movement, is possible to move at both sides of the straight line, and is made so as to be sufficiently fallen out to the outside of the proton irradiation range.

While the collimator for radiation therapy limiting pixel in the form of multi-layer for maximizing the radiation treatment effects according to the present invention has been described with reference to the particular illustrative drawings, the present invention is not restricted by the Examples and Drawings disclosed, and the various modifications can be naturally made by those skilled in the art within the scope of the technical sprit of the present invention.

THE INDUSTRIAL APPLICABILITY

The present invention can be usefully utilized as the collimator for flow pixel proton therapy wherein the manufacturing mode of the damper and compensator which was manufactured by hand is modified with the reverse collimation mode via the collimator by laminating the spread panels at the interval necessary for the spread in Bragg-peak to determine the damper interval and its shape via the program, and to apply it to the treatment of the tumor.

The invention claimed is:

1. A collimator for flow pixel proton therapy comprising an irradiation region which controls an intensity of an irradiated proton, which is characterized in that a plurality of micro-motors arranged at both sides of a main frame and a plurality of spread panels arranged in a center opening of the main frame are connected to each other, one to one, by a corresponding one of a plurality of elastic reels, in which a first half of said plurality of spread panels are moved to a first side of the main frame and a second half of said plurality of spread panels are moved to a second side of the main frame by the opposite micro-motors when a corresponding elastic reel is wound, and in which each of said plurality of spread panels are in a stress release state when the corresponding elastic reel is unwound.

2. The collimator for flow pixel proton therapy according to claim 1, which is characterized in that the center opening of the main frame comprises a proton irradiation range, further including a first connection frame connected at said first side of the main frame and a second connection frame connected at said second side of the main frame, and a plurality of micro-motors arranged and supported by a plurality of supporters that are connected to the first and second connection frames at said first and second sides of the main frame, and the spread panel comprising a pixel form arranged behind said center opening of the main frame is connected by the elastic panel, and each micro-motor is controlled by a controller to allow winding and unwinding of the elastic reels to selectively move the spread panels in the pixel form arranged behind said center opening of the main frame.

3. The collimator for flow pixel proton therapy according to claim 2, which is characterized in that each of said plurality of supporters is connected between a top and a bottom of a corresponding connection frame forming a first plurality of supporters on said first side of the main frame and a second plurality of supporters on said second side of the main frame, and wherein said plurality of micro-motors are distributed along said plurality of supporters at said first and second sides of the main frame, wherein each of plurality of elastic reels connects a motor axis of each of the plurality of micro-motors to each of the plurality of spread panels.

4. The collimator for flow pixel proton therapy according to claim 2, which is characterized in that further comprising a first reel guide installed on said first connection frame and a second reel guide installed on said second connection frame, each for a tension of the plurality of elastic reels.

5. The collimator for flow pixel proton therapy according to claim 2, which is characterized in that each of the micro-motors and each of the plurality of spread panels moved by the elastic reel are allowed to move to one of said first and second sides of the main frame and outside of the center opening of the main frame.

6. The collimator for flow pixel proton therapy according to claim 2, which is characterized in that the elastic reel is comprised of a material which is not affected by a reaction of a radiation of the proton.

7. The collimator for flow pixel proton therapy according to claim 2, which is characterized in that the controller comprises a logic circuit coupled to a driving circuit and controlled by a program, wherein each of the plurality of micro-motors moves a corresponding spread panel upon receiving a signal from said driving circuit.

8. The collimator for flow pixel proton therapy according to claim 2, which is characterized in that the micro-motor comprises a first motor axis on a first side of the micro-motor and a second motor axis on a second side of the micro-motor to connect the spread panel between the first and second motor axes and the spread panel by two (2) of said plurality of elastic reels, and wherein an outer circumference of each motor axis comprises a saw tooth shape.

9. A multi-layered collimator for flow pixel proton therapy, comprising:
a plurality of collimators laminated together, each comprising a plurality of micro-motors arranged at both sides of a main frame and a plurality of spread panels arranged in a center opening of the main frame are connected to each other, one to one, by a corresponding one of a plurality of elastic reels, in which a first half of said plurality of spread panels are moved to a first side of the main frame and a second half of said plurality of spread panels are moved to a second side of the main frame by the opposite micro-motors when a corresponding elastic reel is wound, and in which each of said plurality of spread panels are in a stress release state when the corresponding elastic reel is unwound; and
wherein the center openings of each of said plurality of collimators are aligned with each other.

10. The multi-layered collimator of claim 9, wherein said plurality of micro-motors of each of said plurality of collimators are separately controlled to move corresponding ones of said plurality spread panels to form different irradiation regions for each of said plurality of collimators.

* * * * *